(12) United States Patent
Kim et al.

(10) Patent No.: US 11,819,349 B2
(45) Date of Patent: Nov. 21, 2023

(54) X-RAY IMAGING DEVICE FOR MINIMALLY INVASIVE SURGERY

(71) Applicants: Korea University Research and Business Foundation, Seoul (KR); SEOUL NATIONAL UNIVERSITY R&DB FOUNDATION, Seoul (KR)

(72) Inventors: Hyun-Koo Kim, Seoul (KR); Jae-Sung Lee, Seoul (KR)

(73) Assignees: Korea University Research and Business Foundation, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 286 days.

(21) Appl. No.: 15/573,251

(22) PCT Filed: May 9, 2016

(86) PCT No.: PCT/KR2016/004798
§ 371 (c)(1),
(2) Date: Jun. 22, 2018

(87) PCT Pub. No.: WO2016/182281
PCT Pub. Date: Nov. 17, 2016

(65) Prior Publication Data
US 2019/0038242 A1 Feb. 7, 2019

(30) Foreign Application Priority Data
May 11, 2015 (KR) .......................... 10-2015-0065344

(51) Int. Cl.
*A61B 6/00* (2006.01)
*A61B 17/29* (2006.01)
(Continued)

(52) U.S. Cl.
CPC ............ *A61B 6/4057* (2013.01); *A61B 6/425* (2013.01); *A61B 6/4405* (2013.01);
(Continued)

(58) Field of Classification Search
CPC ..... A61B 6/4057; A61B 6/425; A61B 6/4405; A61B 6/4452; A61B 6/50; A61B 7/29;
(Continued)

(56) References Cited

U.S. PATENT DOCUMENTS 5,637,110 A * 6/1997 Pennybacker ..... A61B 18/1445
606/49
2001/0016750 A1 * 8/2001 Malecki ........... A61B 17/00234
606/205
(Continued)

FOREIGN PATENT DOCUMENTS

CN 102335013 B * 6/2013
DE 102010061880 A1 * 5/2012 ........... A61B 1/3132
(Continued)

OTHER PUBLICATIONS

International Search Report dated Sep. 21, 2016 in corresponding International Patent Application No. PCT/KR2016/004798 (3 pages in English, 3 pages in Korean).

*Primary Examiner* — Katherine L Fernandez
*Assistant Examiner* — Brooke Lyn Klein
(74) *Attorney, Agent, or Firm* — NSIP Law

(57) ABSTRACT

The present invention relates to an X-ray imaging device for minimally invasive surgery, the device including: a rod having a clamp module disposed at a first end of the rod and including a first clamp body, a second clamp body, and a clamp support; an X-ray emission module; an X-ray sensing module; and a manipulation module, in which the rod is inserted into the human body, X-rays are emitted from the X-ray emission module with the first end of the first clamp (Continued)

body and the first end of the second clamp body open with a lesion positioned therebetween in the human body, and the X-rays travel through the lesion and is then sensed by the X-ray sensing module.

6 Claims, 8 Drawing Sheets

(51) Int. Cl.
  *A61B 17/00* (2006.01)
  *A61B 17/28* (2006.01)
(52) U.S. Cl.
  CPC .............. *A61B 6/4452* (2013.01); *A61B 6/50* (2013.01); *A61B 17/29* (2013.01); *A61B 17/2909* (2013.01); *A61B 2017/00809* (2013.01); *A61B 2017/2825* (2013.01); *A61B 2017/2929* (2013.01); *A61B 2017/2932* (2013.01)
(58) Field of Classification Search
  CPC ......... A61B 17/2909; A61B 6/03; A61B 6/00; A61B 2090/376; A61B 6/4429; A61B 6/4458; A61B 6/447; H05G 1/00; G03B 42/00; G03B 42/02; H01J 35/32
  USPC ........................................................ 604/425
  See application file for complete search history.

(56) References Cited

U.S. PATENT DOCUMENTS

| | | | |
|---|---|---|---|
| 2001/0021859 A1* | 9/2001 | Kawai | A61B 17/29 606/205 |
| 2003/0013960 A1* | 1/2003 | Makin | A61B 8/12 600/439 |
| 2005/0203331 A1 | 9/2005 | Szapucki et al. | |
| 2007/0038115 A1* | 2/2007 | Quigley | A61N 7/02 600/471 |
| 2007/0078459 A1* | 4/2007 | Johnson | A61B 17/320016 606/51 |
| 2008/0283576 A1* | 11/2008 | Boyden | A61B 17/068 227/180.1 |
| 2011/0124961 A1* | 5/2011 | Zimmon | A61B 1/00002 600/104 |
| 2012/0271230 A1* | 10/2012 | Amal | A61B 17/122 604/93.01 |
| 2014/0107697 A1* | 4/2014 | Patani | A61B 17/282 606/208 |
| 2014/0341346 A1* | 11/2014 | Lee | A61B 6/145 378/62 |
| 2016/0030077 A1* | 2/2016 | Durvasula | A61B 90/30 600/249 |

FOREIGN PATENT DOCUMENTS

| | | |
|---|---|---|
| KR | 101468182 B1 * | 12/2014 |
| WO | WO 2012/051188 A2 | 4/2012 |

* cited by examiner

X-RAY IMAGING DEVICE FOR MINIMALLY INVASIVE SURGERY

TECHNICAL FIELD

The present invention relates to an X-ray imaging device for minimally invasive surgery, the device being able to minimize a radiation exposure dose with a simple structure when visually checking a lesion using X-rays in laparoscopic surgery or thoracoscopic surgery.

BACKGROUND ART

The average span of human life is increasing with the development of the economy and medical technology, but the rates of most cancers including lung cancer have been increasing as age increases, according to statistics by National Health Insurance Service and Ministry of Health and Welfare of Korea in 2007.

As such, more people are being operated on for lung cancer as early diagnosis is generally applied, but most people who are diagnosed with lung cancer are elderly patients having an early stage of cancer.

Since most elderly cancer patients also have various other complications such as cardiovascular disease, there is a need for a patient-fit limited pneumonectomy that can minimize complications after surgery and improve the quality of patients' life rather than applying the same surgery to all patients.

Recently, for an early cancer with a tumor less than 2 cm and with no spread to a lymph node, limited pneumonectomy such as segmentectomy or lung wedge lobectomy has been attempted rather than thoracoscopy in order to improve the quality of patients' life after surgery by preserving as much of a normal lung as possible.

In order to check lung cancer from a solitary pulmonary nodule, CT-guided percutaneous or bronchoscopic needle aspiration biopsy using chest CT or bronchoscopy is the most sure method, but it is impossible to perform CT-guided percutaneous or bronchoscopic needle aspiration biopsy for a solitary pulmonary nodule of 10 mm or less, ground glass opacity, or a solitary pulmonary nodule close to a blood vessel or important organs.

Most solitary pulmonary nodules found by early diagnosis such as chest CT are small or have ground glass opacity, so it is impossible to apply chest TC or bronchoscopy. In these cases, definitive diagnosis is possible only through a surgical operation of excising a solitary pulmonary nodule.

Recently, The Society of Thoracic Surgeons (STS) recommends surgically excising a solitary pulmonary nodule less than lcm in chest CT when the solitary pulmonary nodule changes in size or shape, so cardiac surgeons have to perform more surgical excisions for diagnosing or treating small solitary pulmonary nodules.

Minimally invasive surgery using a video thoracoscope is a more reasonable method than thoracotomy in order to excise small solitary pulmonary nodules, but most surgeons cannot see and touch with hands solitary pulmonary nodules during a video thoracoscopic surgery in comparison to thoracotomy because solitary pulmonary nodules are inside a lung parenchyma, so surgeons have to perform localization or marking to mark the lesions so that the lesion can be seen for excision.

In limited pneumonectomy such as segmentectomy for a early lung cancer, it is important to maintain an appropriate resection margin from lung cancer in order to reduce local reappearance, and generally, it is required to maintain a resection margin as large as lung cancer or 2 cm from lung cancer Further, it is important to maintain an appropriate resection margin even in limited pneumonectomy for a metastatic lung cancer, so it is required to visually ensure a resection margin from lung cancer during operation by performing localization or marking for visually showing the portion to excise before the operation.

At present, in various localizations for solitary pulmonary nodules, a method of injecting lipiodol and using the C-arm disclosed in Japanese Patent Application Publication No. 2005-58309.

However, the C-Arm has the advantage that it is possible to visually discriminate an accurate resection margin from a solitary pulmonary nodule, but it requires a large X-ray imaging device during an operation, so the operation room is cluttered and there is a possibility of medical staff being exposed to excessive radiation.

International Commission on Radiological Protection (ICRS) has recommended the maximum level of 20 mSv for medical workers, but there is a report that medical workers are exposed to radiations maximally up to 20.88 mSv a year (KIM, Ji-Wan, Journal of The Korean Orthopedic Association, 2010), so there is an X-ray imaging device than can minimize the radiation exposure dose during an operation by the C-Arm and occupy a small space.

DISCLOSURE

Technical Problem

Accordingly, the present invention has been made in an effort to solve the problems and an object of the present invention is to provide an X-ray imaging device for minimally invasive surgery, the device being able to solve the problem that an operation room is cluttered due to equipment by minimizing equipment for visually checking a lesion using X-rays and to minimize a radiation exposure dose in minimally invasive surgery such as laparoscopic surgery or thoracoscopic surgery.

Technical Solution

The present invention provides an X-ray imaging device for minimally invasive surgery, the device including: a rod having a predetermined length that can be inserted into a human body; a clamp module disposed at a first end of the rod and including a first clamp body, a second clamp body, and a clamp support supporting at least one of the first clamp body and the second clamp body such that a first end of the first clamp body and a first end of the second clamp body open and close; an X-ray emission module disposed at the first end of the first clamp body and emitting X-rays to the first end of the second clamp body; an X-ray sensing module disposed at the first end of the second clamp and sensing the X-rays emitted from the X-ray emission module; and a manipulation module disposed at a second end of the rod and operating the clamp module to open and close the first end of the first clamp body and the second end of a second clamp body of the clamp module, in which the rod is inserted into the human body, X-rays are emitted from the X-ray emission module with the first end of the first clamp body and the first end of the second clamp body open with a lesion positioned therebetween in the human body, and the X-rays travel through the lesion and is then sensed by the X-ray sensing module.

The clamp support may support any one of the first clamp body and the second clamp body to be rotatable such that any one of the first clamp body and the second clamp body moves toward and away from the other one, and any one of the first clamp body and the second clamp body may be rotated by the manipulation module.

The clamp support may elastically support the first clamp body and the second clamp body to open the first end of the first clamp body and the first end of the second clamp body, and the manipulation module may operate the clamp module to move the clamp module between an insertion position, where the first end of the first clamp body and the first end of the second clamp body are closed and inserted in the rod from the first end of the rod, and an image position where the clamp module is exposed outside the rod with the first end of the first clamp body and the first end of the second clamp body open by elasticity of the clamp support.

The clamp support may support second ends of the first clamp body and the second clamp body to be rotatable such that the first end of the first clamp body and the first end of the second clamp body open and close, the manipulation module may operate the clamp module to move the clamp module between an insertion position, where the first end of the first clamp body and the first end of the second clamp body are closed and inserted in the rod from the first end of the rod, and an image position where the clamp module is exposed outside the rod, and the first end of the first clamp body and the first end of the second clamp body may be opened by pulling wires connected to the first clamp body and the second clamp body, respectively, at the imaging position.

The clamp module may further include a stopper stopping the first clamp body and the second clamp body with a predetermined distance therebetween when the wires are pulled.

When the first end of the first clamp body and the first end of the second clamp body are open, the X-ray emission module and the X-ray sensing module may be aligned to face each other.

Advantageous Effects

According to the X-ray imaging device for minimally invasive surgery of the present invention, it is possible to solve the problem the an operation room is cluttered due to equipment by minimizing equipment for visually checking a lesion using X-rays and to minimize a radiation exposure dose in minimally invasive surgery such as laparoscopic surgery or thoracoscopic surgery.

BEST MODE

The present invention relates to an X-ray imaging device for minimally invasive surgery, the device including: a rod having a predetermined length that can be inserted into a human body; a clamp module disposed at a first end of the rod and including a first clamp body, a second clamp body, and a clamp support supporting at least one of the first clamp body and the second clamp body such that a first end of the first clamp body and a first end of the second clamp body open and close; an X-ray emission module disposed at the first end of the first clamp body and emitting X-rays to the first end of the second clamp body; an X-ray sensing module disposed at the first end of the second clamp and sensing the X-rays emitted from the X-ray emission module; and a manipulation module disposed at a second end of the rod and operating the clamp module to open and close the first end of the first clamp body and the second end of a second clamp body of the clamp module, in which the rod is inserted into the human body, X-rays are emitted from the X-ray emission module with the first end of the first clamp body and the first end of the second clamp body open with a lesion positioned therebetween in the human body, and the X-rays travel through the lesion and is then sensed by the X-ray sensing module.

Mode for Invention

Hereinafter, the present invention will be described in detail with reference to the accompanying drawings showing embodiments of the present invention.

An X-ray imaging device 100 for minimally invasive surgery according to the present invention is inserted into a human body and takes an X-ray image of a target organ L such as a lung in minimally invasive surgery such as a laparoscopic surgery a thoracoscopic surgery.

Figure 1:
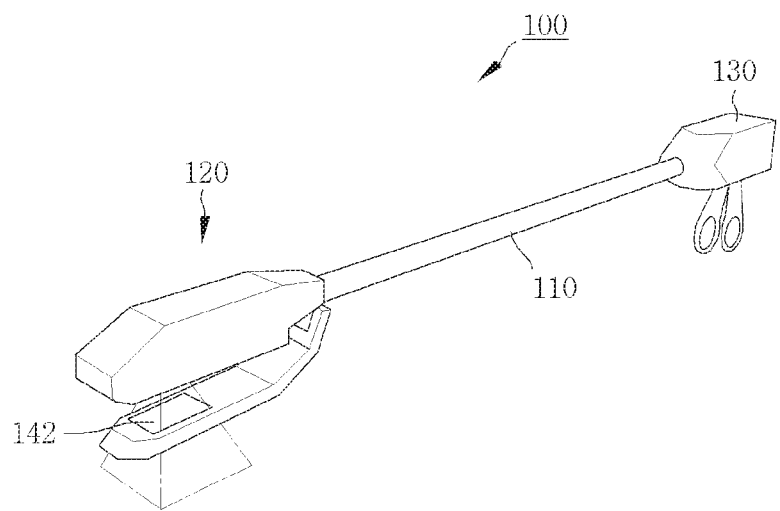
FIG. 1 is a view showing an X-ray imaging device for minimally invasive surgery according to a first embodiment of the present invention.
Figure 2:
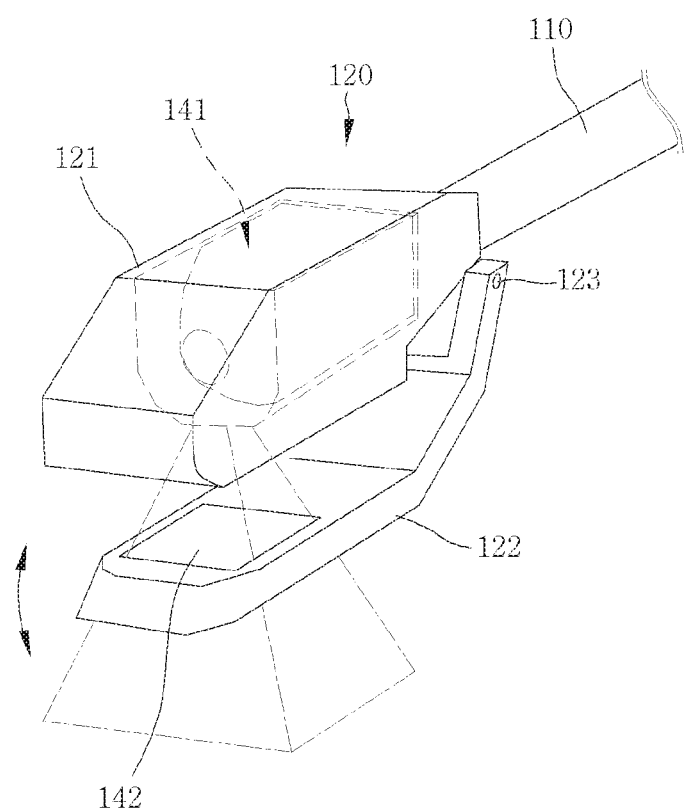
FIG. 2 is a cross-sectional view enlarging a clamp module of the X-ray imaging device for minimally invasive surgery shown in FIG. 1.

FIG. 1 is a view showing an X-ray imaging device 100 for minimally invasive surgery according to a first embodiment of the present invention and FIG. 2 is a view enlarging a clamp module 120 of the X-ray imaging device for minimally invasive surgery shown in FIG. 1.

Referring to FIGS. 1 and 2, the X-ray imaging device for minimally invasive surgery according to the first embodiment of the present invention includes: a rod 110, a clamp module 120, an X-ray emission module 141, and X-ray sensing module 142, and a manipulation module 130.

It is exemplified that the rod 110 has a predetermined length that can be inserted into the a patient's body, and has a substantially cylindrical shape. The clamp module 120 is disposed at a first end, that is, an end to be inserted into a patient's body, of the rod 110 and the manipulation module 130 for operating the clamp module 120 is disposed at a second end.

The clamp module 120, as shown in FIG. 2, is disposed at the first end of the rod 110 and may include a first clamp body 121, a second clamp body 122, and a clamp support 123. The first clamp body 121 and the second clamp body 122 are supported by the clamp support 123 such that a first end of the first clamp body 121 and a second end of the second clamp body 122 can open and close like tongs.

The X-ray emission module 141 is disposed at the first end of the first clamp body 121. The X-ray sensing module 142 is disposed at the second end of the second clamp body 122. When the first end of the first clamp body 121 and the first end of the second clamp body 122 are open, as shown in FIG. 2, the X-ray emission module 141 and the X-ray sensing module 142 are aligned to face each other, so the X-ray sensing module 142 can sense X-rays emitted from the X-ray emission module 141, which will be described below.

In the first embodiment of the present invention, it is exemplified that the first clamp body 121 is fixed to the first end of the rod 110 and the second clamp body 122 is supported rotatably on the first clamp body 121 by the clamp support 123 that is a rotary shaft. Further, it is exemplified that the X-ray emission module 141 is disposed in the first clamp body 121 to emit X-rays to the X-ray sensing module 142 on the second clamp body 122.

Further, the X-ray emission module 141 and the X-ray sensing module 142 are connected to a control equipment such a computer disposed outside through a signal cable (not shown) or a power cable (not shown). The signal cable or the power cable is connected to the X-ray emission module 141 and the X-ray sensing module 142 and connected to the external control equipment through the inside of the rod 110.

The manipulation module 130 is disposed at the second end of the rod 110 and operates the second clamp body 122 of the clamp module 120 to open and close the first end of the first clamp body 121 and the first end of the second clamp body 122 of the clamp module 120.

A method of imaging a lesion T on an organ L such as a lung inside a patient's body using the X-ray imaging device 100 having this configuration for minimally invasive surgery according to the present invention is described hereafter.

First, an operator inserts the rod 110 into a patient's body with the first clamp body 121 and the second clamp body 122 of the clamp module 120 closed, opens the second clamp body 122 away from the first clamp body 121 by manipulating the manipulation module 130 around the organ L such as a lung to be imaged, and then moves the rod 110 such that the target organ L is positioned between the first clamp body 121 and the second clamp body 122, for example, the lesion T is positioned between the first clamp body 121 and the second clamp body 122.

Thereafter, the operator controls the X-ray emission module 141 through the control equipment to emit X-rays, then the X-rays emitted from the X-ray emission module 141 travel through the lesion T and the organ L and are sensed by the X-ray sensing module 142 and the sensing result by the X-ray sensing module 142 is transmitted to the external control equipment through the signal cable, whereby it is possible to see an X-ray image through a monitor of the control equipment.

After finishing the operation, the operator closes the first clamp body 121 and the second clamp body 122 by manipulating the manipulation module 130, and accordingly, the operator can pull the rod 110 out of the patient's body.

Since the clamp module 120 according to an embodiment of the present invention is formed like tongs such that the first clamp body 121 and the second clamp body 122 open and close, as described above, it is possible to hold a tissue such as a lung by closing the first clamp body 121 and the second clamp body 122. Accordingly, when performing minimally invasive surgery using the X-ray imaging device 100 for minimally invasive surgery according to the present invention, it is possible to take an X-ray image, if necessary, while using the X-ray imaging device 100 for minimally invasive surgery as a gripper, without using a separate gripper for holding a tissue etc.

This configuration can be achieved in a size that can be inserted into a patient's body to obtain an X-ray image in minimally invasive surgery, so the environment of an operation room can be simplified. Further, it is possible to remarkably reduce a radiation exposure dose due to X-rays that are radiated to other parts of a patient when emitted around the lesion T in the patient's body, or that are radiated to an operator.

Further, when a lung is excavated to image and perform an operation thereon, the volume of the lung is decreased (see FIG. 5), so even if the gap between the first clamp body 121 and the second clamp body 122 is not large, it is possible to take an X-ray image with the lung between the clamp bodies. Accordingly, an X-ray image can be obtained even by the structure of the clamp module 120 according to the first embodiment of the present invention.

Figure 3:
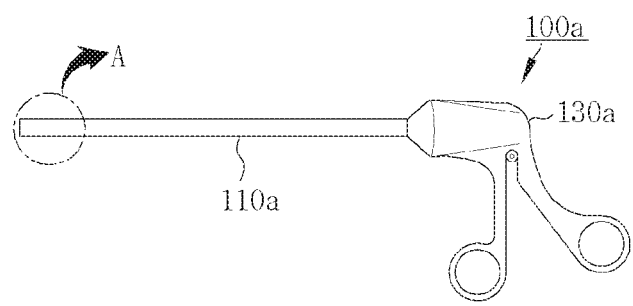
FIG. 3 is a view showing an X-ray imaging device for minimally invasive surgery according to a second embodiment of the present invention.
Figure 4:
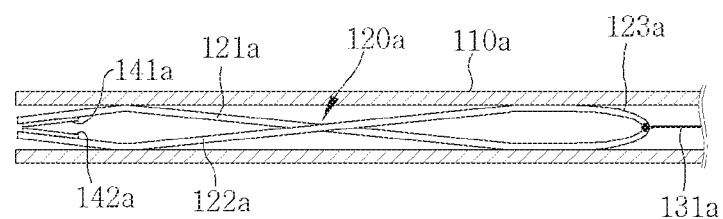
FIG. 4 is an enlarged view of the area A in FIG. 3.
Figure 5:
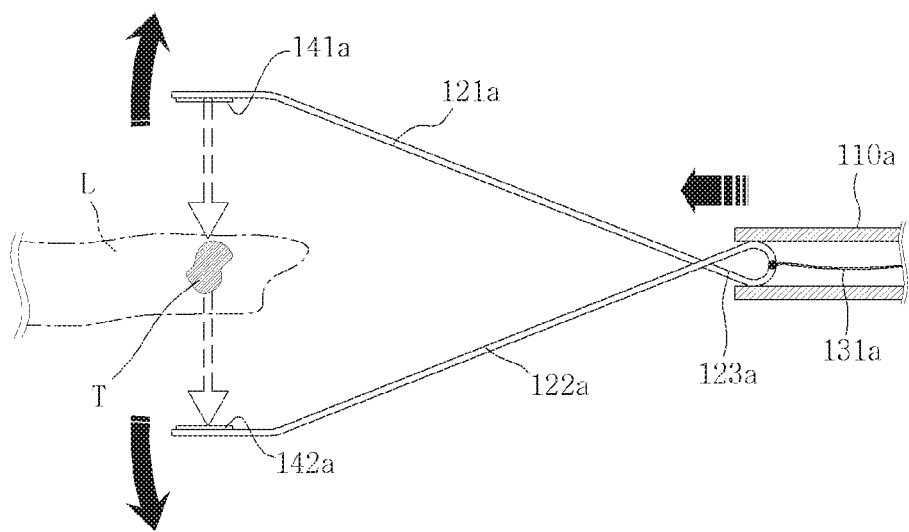
FIG. 5 is a view showing the operation of a clamp module of the X-ray imaging device for minimally invasive surgery according to the second embodiment of the present invention.

An X-ray imaging device 100a for minimally invasive surgery according to a second embodiment of the present invention is described hereafter in detail with reference to FIGS. 3 to 5.

Referring to FIGS. 3 and 5, the X-ray imaging device 100a for minimally invasive surgery according to the second embodiment of the present invention includes: a rod 110a, a clamp module 120a, an X-ray emission module 141a, and an X-ray sensing module 142a, and a manipulation module 130a.

It is exemplified that the rod 110a, the same as in the first embodiment, has a predetermined length that can be inserted into a patient's body, and has a substantially cylindrical shape. The clamp module 120a is disposed at a first end, that is, an end to be inserted into a patient's body, of the rod 110a and the manipulation module 130a for operating the clamp module 120a is disposed at a second end.

The clamp module 120a, as shown in FIGS. 4 and 5, is disposed at the first end of the rod 110a and may include a first clamp body 121a, a second clamp body 122a, and a clamp support 123a. The first clamp body 121a and the second clamp body 122a are supported by the clamp support 123a such that a first end of the first clamp body 121a and a second end of the second clamp body 122a can open and close like tongs.

As in the first embodiment, the X-ray emission module 141a is disposed at the first end of the first clamp body 121a. The X-ray sensing module 142a is disposed at the second end of the second clamp body 122a. When the first end of the first clamp body 121a and the first end of the second clamp body 122a are open, as shown in FIG. 5, the X-ray emission module 141a and the X-ray sensing module 142a are aligned to face each other, so the X-ray sensing module 142a can sense X-rays emitted from the X-ray emission module 141a. The X-ray emission module 141a and the X-ray sensing module 142a can be connected to control equipment such as a computer disposed outside through a signal cable (not shown) or a power cable (not shown).

The manipulation module 130a is disposed at the second end of the rod 110a and operates the clamp module 120a to open and close the first end of the first clamp body 121a and the first end of the second clamp body 122a of the clamp module 120a.

It is exemplified that clamp support 123a according to the second embodiment of the present invention, as shown in FIGS. 4 and 5, elastically supports the first end of the first clamp body 121a and the second clamp body 122a to open the first end of the first clamp body 121a and the first end of the second clamp body 122a.

The first clamp body 121a, second clamp body 122b, and clamp support 123a are integrally formed in FIGS. 4 and 5, the first clamp body 121a and the second clamp body 122a are elastically closed, as shown in FIG. 5, and are then inserted into the rod 110, as shown in FIG. 4.

The first clamp module 120a is moved by the manipulation module 130a between an insertion position in the rod 110a shown in FIG. 4 and an imaging position exposed outside the rod 110a.

In detail, at the insertion position, as shown in FIG. 4, the clamp module 120a is inserted in the rod 110a with the first end of the first clamp body 121a and the first end of the second clamp body 122a closed against the elasticity of the clamp support 123a.

Further, at the imaging position, as shown in FIG. 5, the clamp module 120a is exposed outside the rod 110a with the first end of the first clamp body 121a and the first end of the second clamp body 122a open by the elasticity of the clamp support 123a.

A method of imaging a lesion T on an organ L such as a lung inside a patient's body using the X-ray imaging device 100a having this configuration for minimally invasive surgery according to the second embodiment of the present invention is described hereafter.

First, the operator inserts the rod 110a into a patient's body with the clamp module 120a at the insertion position and then exposes the clamp module 120a outside the rod 110a by manipulating the manipulation module 130a around a target organ L such as a lung. Accordingly, the first end of the first clamp body 121a and the first end of the second clamp body 122a are opened by the elasticity of the clamp support 123a of the clamp module 120a at the insertion position shown in FIG. 5.

Thereafter, the operator, as shown in FIG. 5, moves the first clamp body 121a and the second clamp body 122a around the organ L such as a lung such that the target lesion T is positioned between the X-ray emission module 141a at the first end of the first clamp body 121 and the X-ray sensing module 142a at the first end of the second clamp body 122a.

Thereafter, the operator controls the X-ray emission module 141a through the control equipment to emit X-rays, then the X-rays emitted from the X-ray emission module 141a travel through the lesion T and the organ L and is sensed by the X-ray sensing module 142a and the sensing result by the X-ray sensing module 142 is transmitted to the external control equipment through the signal cable, whereby it is possible to see an X-ray image through a monitor of the control equipment.

After finishing the surgery, the operator pulls the clamp module 120a by manipulating the manipulation module 130a, then the first clamp body 121a and the second clamp body 122a are closed and inserted into the rod 110a to the insertion position shown in FIG. 3. Accordingly, the operator can pull the rod 110a out of the patient's body.

In the second embodiment of the present invention, as shown in FIGS. 4 and 5, it is exemplified that a rigid operation wire 131a is connected to the manipulation module 130a and the clamp module 120a to move the clamp module 120a between the insertion position and the imaging position, but other structures that move the clamp module 110a in the longitudinal direction of the rod 110a may be applied.

Figure 6:
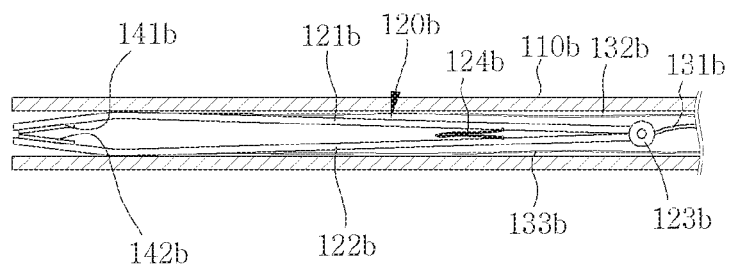
FIGS. 6 to 8 are views showing the operation of a clamp module of the X-ray imaging device for minimally invasive surgery according to a third embodiment of the present invention.
Figure 7:
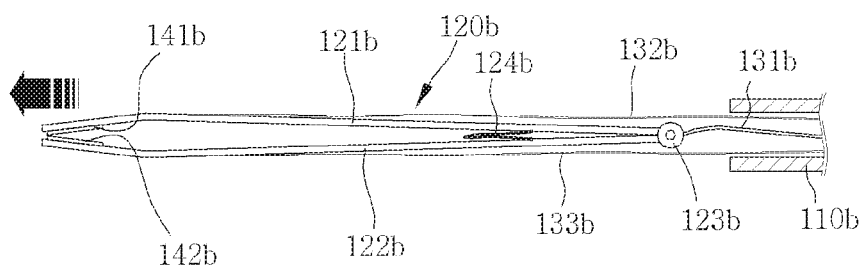
Figure 8:
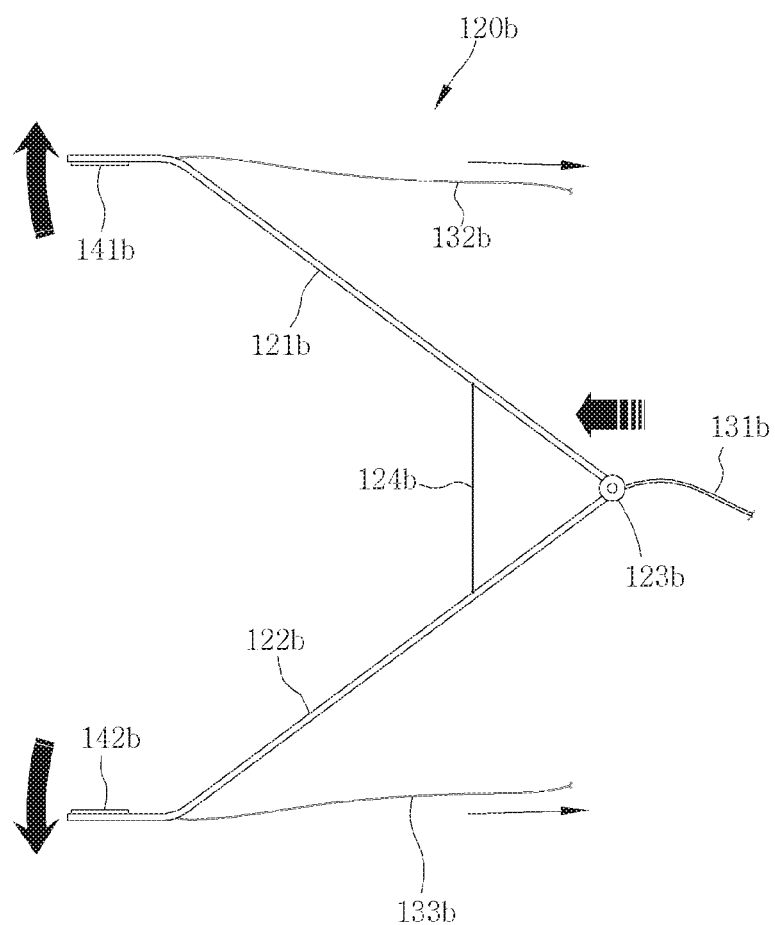

An X-ray imaging device 100a for minimally invasive surgery according to a third embodiment of the present invention is described hereafter in detail with reference to FIGS. 6 to 8. The fundamental configuration of the X-ray imaging device 100a for minimally invasive surgery according to a third embodiment of the present invention corresponding to that of the second embodiment, except for a clamp module 120b shown in FIGS. 6 to 8. Reference numerals not shown in FIGS. 6 to 8 refer to the reference numerals of corresponding components in the second embodiment.

A clamp support 123b of the clamp module 120b according to the third embodiment supports second ends of a first clamp body 121b and second clamp body 122b such that a first end of the first clamp body 121b and a first end of the second clamp body 122b open and close.

A manipulation module 130a operates the clamp module 120b between an insertion position where the first end of the first clamp body 121b and the first end of the second clamp body 122b are closed and inserted in a rod 110b from an end of the rod 110b (see FIG. 6) and an imaging position where the clamp module 120b is exposed outside the rod 110b (see FIG. 7).

An operator pulls clamp wires 132b and 133b connected to the first clamp body 121b and the second clamp body 122b, respectively, at the imaging position toward the manipulation module 130a, as shown in FIG. 8, thereby opening the first end of the first clamp body 121b and the first end of the second clamp body 122b.

The clamp module 120b may include a stopper 124b that stops the first clamp body 121b and the second clamp body 122b with an X-ray emission module 141b and an X-ray sensing module 142 facing each other when the clamp wires 132b and 133b are pulled. According to the present invention, as shown in FIG. 8, the stopper 124b may be a wire connecting the first clamp body 121b and the second clamp body 122b to each other to stop the first clamp body 121b and the second clamp body 122b with a predetermined distance therebetween.

Although embodiments of the present invention were described above, it would be understood by those skilled in the art that the embodiments may be modified without departing from the spirit and scope of the present invention. The scope of the present invention should be determined by claims and equivalents of the claims.

REFERENCE NUMERALS 100, 100a: X-ray imaging device for minimally invasive surgery
110, 110a, 110b: rod 120, 120a, 120b: clamp module
121, 121a, 121b: first clamp body 122, 122a, 122b: second clamp body
123, 123a, 123b: clamp support 124b: stopper
130, 130a: manipulation module 131a, 131b: operation wire
132b, 133b: clamp wire 141, 141a, 141b: X-ray emission module
142, 142a, 142b: X-ray sensing module

INDUSTRIAL APPLICABILITY

The present invention can be applied to visually checking a lesion using an X-ray in minimally invasive surgery such as a laparoscopic surgery and a thoracoscopic surgery.

The invention claimed is:
1. An X-ray imaging device for minimally invasive surgery, the device comprising:
a rod having a predetermined length that can be inserted into a human body; a clamp module disposed at a first end of the rod and including a first clamp body, a second clamp body, and a clamp support supporting at least one of the first clamp body and the second clamp body such that a first end of the first clamp body and a first end of the second clamp body open and close;

an X-ray emission module disposed at the first end of the first clamp body;

an X-ray sensing module disposed at the first end of the second clamp;

a first wire connected to the first end of the first clamp body;

a second wire connected to the first end of the second clamp body; and a manipulation module disposed at a second end of the rod and operating the clamp module to open and close the first end of the first clamp body and the first end of the second clamp body of the clamp module, wherein the rod is configured to be inserted into the human body for the minimally invasive surgery comprising a laparoscopic surgery and a thoracoscopic surgery, such that the X-ray emission module and the X-ray sensing module are inserted together into the human body when the rod is inserted into the human body in a state that the first end of the first clamp body and the first end of the second clamp body are closed, wherein X-rays are emitted from the X-ray emission module with the first end of the first clamp body and the first end of the second clamp body in an open state and are configured to position a lesion of a target organ therebetween in the human body, and the emitted X-rays travel through the lesion and are then sensed by the X-ray sensing module for X-ray imaging, and wherein when the first end of the first clamp body and the first end of the second clamp body are in the open state, a surface of the first end of the first clamp body and a surface of the first end of the second clamp body are aligned to face each other in parallel, such that the X-ray emission module and the X-ray sensing module are aligned to face each other, wherein the clamp support supports second ends of the first clamp body and the second clamp body to be rotatable such that the first end of the first clamp body and the first end of the second clamp body open and close, the manipulation module operates the clamp module to move the clamp module between an insertion position, where the first end of the first clamp body and the first end of the second clamp body are closed and inserted in the rod from the first end of the rod, and an image position where the clamp module is exposed outside the rod, and the first end of the first clamp body and the first end of the second clamp body are opened by pulling the first wire and the second wire, respectively, in a proximal direction toward the manipulation module at the image position.

2. The device of claim 1, wherein the clamp module further includes a stopper stopping the first clamp body and the second clamp body with a predetermined distance therebetween when the first and second wires are pulled.

3. The device of claim 1, wherein the first and second clamp bodies are configured to hold an object when closing.

4. The device of claim 1, wherein one of the X-ray emission module and the X-ray sensing module is positioned at one side of an extension line of the rod, and the other of the X-ray emission module and the X-ray sensing module is positioned at the other side of the extension line.

5. An X-ray imaging device for minimally invasive surgery, the device comprising:

a rod having a predetermined length that can be inserted into a human body;

a clamp module disposed at a first end of the rod and comprising a first clamp body, a second clamp body, and a clamp support integrally formed with the first clamp body and the second clamp body and supporting the first clamp body and the second clamp body such that a first end of the first clamp body and a first end of the second clamp body open and close;

an X-ray emission module disposed at the first end of the first clamp body;

an X-ray sensing module disposed at the first end of the second clamp;

a first wire connected to the first end of the first clamp body;

a second wire connected to the first end of the second clamp body; and a manipulation module disposed at a second end of the rod and operating the clamp module to open and close the first end of the first clamp body and the second end of the second clamp body of the clamp module, wherein the rod is configured to be inserted into the human body for the minimally invasive surgery comprising a laparoscopic surgery and a thoracoscopic surgery, such that the X-ray emission module and the X-ray sensing module are inserted together into the human body when the rod is inserted into the human body in a state that the first end of the first clamp body and the first end of the second clamp body are closed, wherein X-rays emitted from the X-ray emission module with the first end of the first clamp body and the first end of the second clamp body in an open state and are configured to position a lesion therebetween in the human body, and the emitted X-rays travel through the lesion and are then sensed by the X-ray sensing module, wherein when the first end of the first clamp body and the first end of the second clamp body are in the open state, a surface of the first end of the first clamp body and a surface of the first end of the second clamp body are aligned to face each other in parallel, such that the X-ray emission module and the X-ray sensing module are aligned to face each other, wherein the first clamp body and the second clamp body cross each other at a first position inside the rod when the first end of the first clamp body and the first end of the second clamp body are closed, and wherein the first clamp body and the second clamp body cross each other at a second position outside the rod when the first end of the first clamp body and the first end of the second clamp body are in the open state, wherein the clamp support supports second ends of the first clamp body and the second clamp body to be rotatable such that the first end of the first clamp body and the first end of the second clamp body open and close, the manipulation module operates the clamp module to move the clamp module between an insertion position, where the first end of the first clamp body and the first end of the second clamp body are closed and inserted in the rod from the first end of the rod, and an image position where the clamp module is exposed outside the rod, and the first end of the first clamp body and the first end of the second clamp body are opened by pulling the first wire and the second wire, respectively, in a proximal direction toward the manipulation module at the image position.

6. The device of claim 5, wherein the clamp module further includes a stopper stopping the first clamp body and the second clamp body with a predetermined distance therebetween when the first and second wires are pulled.

* * * * *